United States Patent
Jensen

(10) Patent No.: US 11,622,835 B1
(45) Date of Patent: Apr. 11, 2023

(54) LASER ENDODONTIC PROCEDURES UTILIZING ALCOHOL BASED INDOCYANINE GREEN SOLUTIONS

(71) Applicant: CAO Group, Inc., West Jordan, UT (US)

(72) Inventor: Steven D. Jensen, South Jordan, UT (US)

(73) Assignee: CAO Group, Inc., West Jordan, UT (US)

( * ) Notice: Subject to any disclaimer, the term of this patent is extended or adjusted under 35 U.S.C. 154(b) by 0 days.

(21) Appl. No.: 17/804,765

(22) Filed: May 31, 2022

(51) Int. Cl.
*A61B 18/20* (2006.01)
*A61C 5/40* (2017.01)
*A61B 18/22* (2006.01)

(52) U.S. Cl.
CPC .............. *A61C 5/40* (2017.02); *A61B 18/22* (2013.01); *A61B 2018/206* (2013.01)

(58) Field of Classification Search
CPC .......... A61C 1/0046; A61C 5/40; A61N 5/06; A61N 5/062; A61N 5/0624; A61B 18/20
See application file for complete search history.

(56) References Cited

U.S. PATENT DOCUMENTS

| 7,306,459 B1* | 12/2007 | Williams ................. A61C 5/50 433/29 |
| 2004/0199227 A1* | 10/2004 | Altshuler ................. A61K 8/02 607/100 |
| 2004/0202982 A1* | 10/2004 | Bornstein .............. A61C 17/20 433/29 |
| 2016/0067149 A1* | 3/2016 | Kishen ..................... A61K 6/20 424/44 |
| 2017/0027647 A1* | 2/2017 | DiVito ................. A61C 1/0046 |
| 2018/0000559 A1* | 1/2018 | Titlebaum .............. A61C 19/06 |

* cited by examiner

*Primary Examiner* — Lynsey C Eiseman
(74) *Attorney, Agent, or Firm* — Dobbin IP Law, P.C.; Geoffrey E. Dobbin

(57) ABSTRACT

A method of endodontic therapy with improved disinfection and ablation characteristics may feature the use of an alcohol or polyol-based indocyanine green (ICG) solution with a laser system that emits a wavelength within the maximal absorption range of ICG. By matching the dye and laser output, radiant energy use is maximized for efficient ablation and disinfection of treated tissues. Also, the use of an alcohol or polyol as a solvent for the ICG solution increases the inherent disinfection qualities of the solution itself. In one embodiment, the prepared canal is flooded with the ICG solution and the laser activates with the laser fiber inserted into the solution. In an alternate embodiment, the solution is mostly removed prior to activation of the laser, but only after necrotic tissue has been stained.

10 Claims, 2 Drawing Sheets

US 11,622,835 B1

LASER ENDODONTIC PROCEDURES UTILIZING ALCOHOL BASED INDOCYANINE GREEN SOLUTIONS

FIELD OF THE INVENTION

The present invention relates to the field of dentistry and more particularly relates to a therapeutic procedure coupling laser treatment with indocyanine green ("ICG") to enhance disinfection and ablation of tissues to be treated.

BACKGROUND OF THE INVENTION

During contemporary root canal therapy treatments there is a need for removing necrotic tissue and disinfecting the canal. The prospect of utilizing a laser to carbonize necrotic tissue and disinfect the canal with radiant energy is of great interest to clinicians because of the apparent "ease of use" it adds to current standard procedures. The possibility of placing a dye into the root canal that is matched to absorb the wavelength of the treatment laser is also of great interest, because it requires the use of a single laser with one wavelength output and there is no need to purchase multiple lasers for different material substrates; since the dye is matched to absorb the treatment lasers radiant energy output it will efficiently lase whatever surface to which the dye is applied.

The present invention has found a synergistic means of easily delivering indocyanine green (ICG) into the root canal while concordantly increasing the penetration into soft tissue, increasing the water chasing efficiency, increasing the staining of necrotic tissue, and increasing the overall anti-microbial effect by the introduction of alcohols into indocyanine green (ICG) solutions. The present invention represents a departure from the prior art in that the methodology efficiently utilizes ICG in conjunction with laser therapy for enhanced treatment.

SUMMARY OF THE INVENTION

In view of the foregoing disadvantages inherent in the known types of endodontic therapy, an improved method of endodontic therapy may provide a solution of ICG which is applied to a treatment area before irradiation of said area by an 810 nm diode laser. The method should meet the following objectives: that it be easy to administer and implement, that it has a degree of familiarity with current methodologies, that the materials be inexpensive to manufacture, that the methodology be effective in both disinfection and as an aid to tissue ablation in an endodontic procedure. As such, a new and improved methodology may comprise the introduction of an organic based ICG solution to a treatment area before irradiation to accomplish these objectives.

The more important features of the invention have thus been outlined in order that the more detailed description that follows may be better understood and in order that the present contribution to the art may better be appreciated. Additional features of the invention will be described hereinafter and will form the subject matter of the claims that follow.

Many objects of this invention will appear from the following description and appended claims, reference being made to the accompanying drawings forming a part of this specification wherein like reference characters designate corresponding parts in the several views.

Before explaining at least one embodiment of the invention in detail, it is to be understood that the invention is not limited in its application to the details of construction and the arrangements of the components set forth in the following description or illustrated in the drawings. The invention is capable of other embodiments and of being practiced and carried out in various ways. Also, it is to be understood that the phraseology and terminology employed herein are for description and should not be regarded as limiting.

As such, those skilled in the art will appreciate that the conception, upon which this disclosure is based, may readily be utilized as a basis for the designing of other structures, methods, and systems for carrying out the several purposes of the present invention. It is important, therefore, that the claims be regarded as including such equivalent constructions insofar as they do not depart from the spirit and scope of the present invention.

BRIEF DESCRIPTION OF THE DRAWINGS

In order to describe the manner in which the above-recited and other advantages and features of the invention can be obtained, a more particular description of the invention briefly described above will be rendered by reference to specific example embodiments thereof which are illustrated in the appended drawings. Understanding that these drawings depict only typical embodiments of the invention and are therefore not to be considered as limiting of its scope, the invention will be described and explained with additional specificity and detail using the accompanying drawings.

DESCRIPTION OF THE PREFERRED EMBODIMENTS

Figure 1:
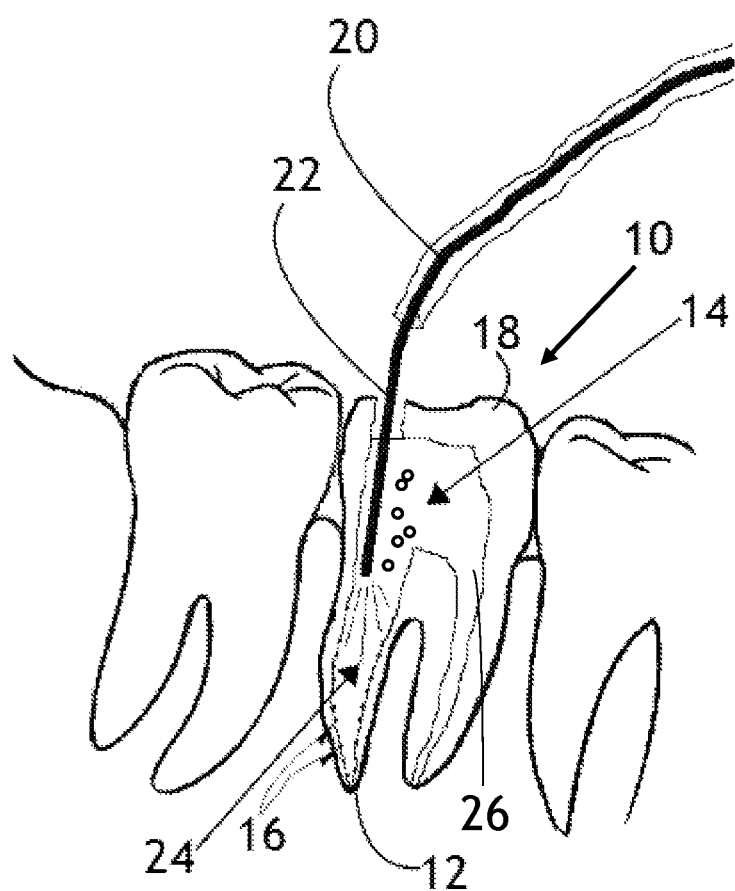
FIG. 1 is a schematic view depicting one embodiment of an endodontic treatment.

Preferred embodiments of the endodontic therapy method are herein described. It should be noted that the articles "a", "an", and "the", as used in this specification, include plural referents unless the content clearly dictates otherwise.

The preferred dye of the present invention is Indocyanine Green (ICG), and the preferred laser is an 810 nm laser, both of which are commercially available. Indocyanine Green has a maximum absorption range between 780-820 nm; therefore, any laser emitting radiant energy within these wavelength parameters would be sufficient to activate Indocyanine Green at relative high efficacy. The readily available 810 nm diode laser is therefore ideally suited to use in this methodology.

Indocyanine Green is soluble in water, alcohols and liquid polyols; however, it is known to be unstable in water. An embodiment of the present invention utilizes mono-alcohols such as: ethyl, methyl, isopropyl, n-propyl, butyl alcohol and any other alcohols that are liquids as the solvent for ICG. Another embodiment of the present invention utilizes polyols (which may be generally categorized with "alcohols" for purposes of this application) such as glycerin, propylene glycol, polyethylene glycols and any other polyols that are liquids. Additional embodiments of the present invention utilize mixtures of organic solvents with and without water to customize individual characteristics for the delivery of soluble ICG such as: capillary action, water chasing efficiency, anti-microbial properties, substrate staining efficacy and other characteristics. A preferred embodiment of the present invention utilizes ethanol as the best choice of alcohol of out of many possible alcohols because of its combined superior attributes namely: low toxicity, excellent water chasing capability, excellent anti-microbial activity, and increased tissue staining properties—especially when staining necrotic tissue.

While many embodiments of the present invention incorporate 100% organic solvents when manufacturing ICG solutions, other embodiments incorporate at least some quantity of water in the formulation. The possible ranges of alcohol to water ratios are:

Most Preferred Formulation Range: 90%-100% alcohols+ %10-0.0% water.

Preferred Formulation Range: 70%-99.9% alcohols+ 30%-0.1% water.

Less Preferred formulation Range: 5%-99% alcohols+ 95%-1% water.

ICG solutions that contain higher ratios of organic solvents to water concentrations become increasingly more combustible when activated by a matching laser, which in turn helps facilitate the disinfection and removal of necrotic tissue in the canal. It is important to note that this is not possible with 100% ICG\water solutions. The organic alcohols that make up the solvent in these ICG solutions burn or conflagrate locally when energized by sufficient radiant energy. The use of an alcohol based ICG solution together with the matched laser creates extreme local ablation within a very short time frame, usually a few seconds. The synergy of the combined effect of the laser, ICG dye, and the organic solvents creates the localized "synergistic firestorm" designed to adequately ablate necrotic tissue and disinfect the canal.

While many embodiments of ICG solutions can be identified, two methodologies of root canal therapy utilizing lasers matched to ICG solutions are found to have additional promise. The first method is designed to flood an extirpated root canal with ICG solution and insert the fiber optic cable tip into the canal while the canal is full of solution. The laser is then activated while the cable tip is submerged within the pooled ICG solution. Radiant energy produced by the laser is transferred to the ICG solution, resulting in localized heat, combustion, cavitation, and the production of secondary light emission.

The preferred treatment method for this embodiment, shown in FIG. 1, is to first gain access to the pulp chamber of the tooth (10) by conventional means such as with a high-speed handpiece, and then extirpate the necrotic root with endodontic files (as per the prior art). After these initial steps, ICG dye solution is introduced into the canal and pooled (26) in the exposed canal (14). Time for the solution to infiltrate residual soft tissues may be provided. After sufficient time has elapsed, which may be no time, an unclad end (22) of a fiber optic (20) connected to the radiant energy source, in this preferred case an 810 nm diode laser, is then inserted into the canal (14) and the 810 nm diode laser initiated. Upon absorption of emitted radiant energy (24), the ICG dye efficiently heats to such an extent that it begins to boil and evaporate. Then, after the solution is evaporated, the laser will burn residual necrotic tissue (16) which has been stained in the presence of the dye. The entire length of the canal (14) is treated from the root apex (12) to the coronal portion of the tooth (18) by slowly moving the tip in and out of the root canal (14) multiple times during the treatment. After laser treatment, the canal (14) may be further treated with an antiseptic rinse, as would also be customary in the prior art, to kill residual pathogens and to rinse combusted tissues from the canal (14).

Figure 2:
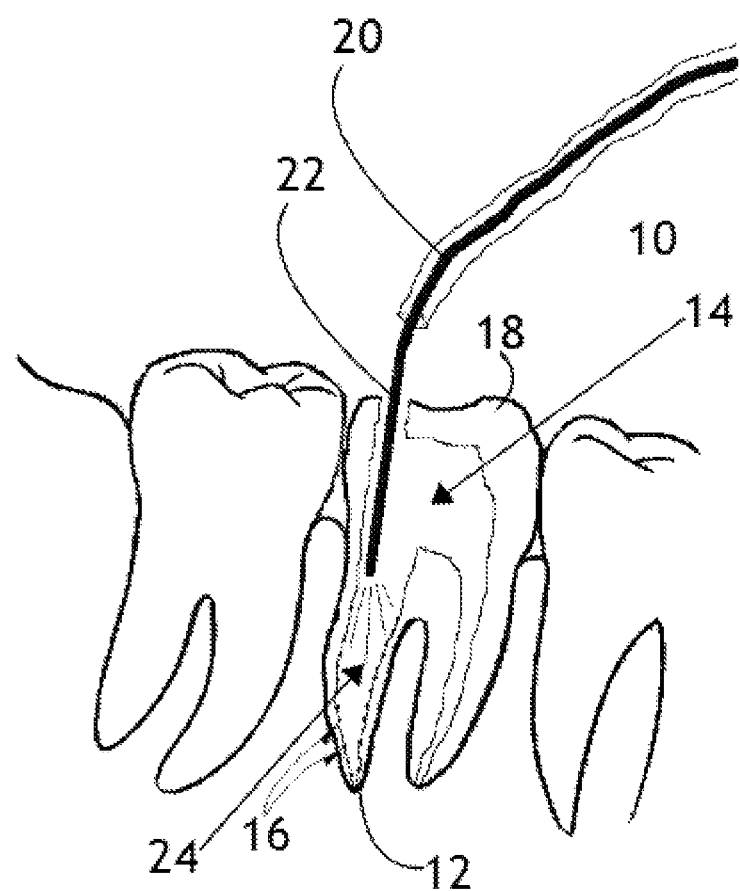
FIG. 2 is an alternate schematic view depicting another embodiment of an endodontic treatment.

The second embodiment of the method (FIG. 2) also first floods the root canal (14) with ICG solution, allowing the solution to penetrate the necrotic tissue (16). After sufficient dwell time, the bulk of the ICG solution is removed with a paper point leaving only a residual amount of ICG solution in the canal (14) and stained necrotic tissue (16). The fiber optic cable tip (22) is then inserted into the dried canal (14) and the laser is activated wherein the radiant energy produced (24) is transferred to the residual ICG solution resulting in localized heat, combustion, carbonization, and the production of secondary light emission. This method of activation produces significantly more local heat than the above first method.

Although the present invention has been described with reference to preferred embodiments, numerous modifications and variations can be made and still the result will come within the scope of the invention. The described embodiments are to be considered in all respects only as illustrative and not restrictive. No limitation with respect to the specific embodiments disclosed herein is intended or should be inferred. Therefore, the scope of the invention is indicated by the appended claims rather than by the foregoing description. All changes which come within the meaning and range of equivalency of the claims are to be embraced within their scope.

What is claimed is:

1. A root canal therapy treatment for removing necrotic tissue and disinfecting the root canal comprising:
   a first step of preparing a root canal, including removing most of the necrotic tissue therefrom and leaving some residual necrotic tissue behind;
   a subsequent step of flooding the canal with a solution of indocyanine green and allowing the solution to pool in the canal;
   a further step of inserting a fiber optic laser tip into the canal such that the tip is submersed in the pooled indocyanine green solution; and
   activating a laser in operative connection with the fiber optic laser tip to emit a laser beam with sufficient radiant energy to evaporate the pooled indocyanine green solution and carbonize the residual necrotic tissue within the canal.

2. The root canal therapy treatment of claim 1, the laser being an 810 nm diode laser.

3. The root canal therapy treatment of claim 1, the solution of indocyanine green utilizing ethanol as a solvent.

4. The root canal therapy treatment of claim 1, the solution of indocyanine green utilizing a solvent, the solvent having a concentration of at least 90% alcohol.

5. The root canal therapy treatment of claim 1, further comprising a step of moving the fiber optic laser tip within the canal while the laser is activated, wherein the canal may be better exposed to the radiant energy of the laser.

6. A root canal therapy treatment for removing necrotic tissue and disinfecting the root canal comprising:
   a first step of preparing a canal, including removing most of the necrotic tissue therefrom and leaving some residual necrotic tissue behind;
   a subsequent step of flooding the canal with a solution of indocyanine green and allowing the solution to pool in the canal;
   a further step of inserting a fiber optic laser tip into the canal such that the tip is submersed in the pooled indocyanine green solution; and
   activating a laser in operative connection with the fiber optic laser tip to emit a laser beam with sufficient radiant energy to evaporate the pooled indocyanine green solution and ablate the residual necrotic tissue within the canal.

7. The root canal therapy treatment of claim 6, the solution of indocyanine green utilizing a solvent, the solvent having a concentration of at least 90% alcohol.

8. The root canal therapy treatment of claim 6, the solution of indocyanine green utilizing ethanol as a solvent.

9. The root canal therapy treatment of claim 6, the laser being an 810nm diode laser.

10. The root canal therapy treatment of claim 6, further comprising a step of moving the fiber optic laser tip within the canal while the laser is activated, wherein the canal may be better exposed to the radiant energy of the laser.

\* \* \* \* \*